United States Patent
Maloisel et al.

(10) Patent No.: US 10,266,563 B2
(45) Date of Patent: Apr. 23, 2019

(54) CHROMATOGRAPHY METHOD

(71) Applicant: GE Healthcare BioProcess R&D AB, Uppsala (SE)

(72) Inventors: Jean-Luc Maloisel, Uppsala (SE); Ola Lind, Uppsala (SE); Bjorn Noren, Uppsala (SE); Ronnie Palmgren, Uppsala (SE)

(73) Assignee: GE Healthcare Bio-Process R&D AB, Uppsala (SE)

( * ) Notice: Subject to any disclaimer, the term of this patent is extended or adjusted under 35 U.S.C. 154(b) by 175 days.

(21) Appl. No.: 15/308,327

(22) PCT Filed: Jun. 4, 2015

(86) PCT No.: PCT/EP2015/062500
§ 371 (c)(1),
(2) Date: Nov. 1, 2016

(87) PCT Pub. No.: WO2015/197338
PCT Pub. Date: Dec. 30, 2015

(65) Prior Publication Data
US 2017/0051010 A1 Feb. 23, 2017

(30) Foreign Application Priority Data
Jun. 24, 2014 (SE) ...................... 1450779

(51) Int. Cl.
| | | |
|---|---|---|
| C07K 1/22 | (2006.01) | |
| C07K 16/00 | (2006.01) | |
| C07K 16/06 | (2006.01) | |
| C07K 1/14 | (2006.01) | |

(52) U.S. Cl.
CPC ............... C07K 1/22 (2013.01); C07K 16/00 (2013.01); C07K 16/065 (2013.01); C07K 1/145 (2013.01); C07K 2317/55 (2013.01)

(58) Field of Classification Search
None
See application file for complete search history.

(56) References Cited

U.S. PATENT DOCUMENTS

| | | | |
|---|---|---|---|
| 6,406,863 B1 * | 6/2002 | Zhu ................. | C07K 16/00 435/29 |
| 2006/0134805 A1 | 6/2006 | Berg et al. | |

FOREIGN PATENT DOCUMENTS

| | | |
|---|---|---|
| WO | 9522389 A1 | 8/1995 |
| WO | 2006/065208 A1 | 6/2006 |
| WO | 2010/005364 A1 | 1/2010 |
| WO | 2011/102790 A1 | 8/2011 |
| WO | 2012/005664 A1 | 1/2012 |
| WO | 2012/134381 A1 | 10/2012 |

OTHER PUBLICATIONS

International Search Report and Written Opinion regarding International Application No. PCT/EP2015/062500, dated Jul. 20, 2015, 9 pages.
International Type Search Report regarding SE Application No. 1450779-2, dated Jan. 27, 2015, 7 pages.
Adsorption and separation of immunoglobulins by novel affinity core-shell beads decorated with Protein L and I-histidine, Gulay Bayramoglu et al., Journal of Chromatography B, vol. 936, Oct. 1, 2013, pp. 1-9.

* cited by examiner

*Primary Examiner* — Stacy B Chen
(74) *Attorney, Agent, or Firm* — Wood IP LLC

(57) ABSTRACT

The present invention relates to a method for removal of large contaminants, such as virus, in a chromatographic process for purification of a target molecule, preferably monoclonal antibodies, mAbs, by using a specifically designed chromatographic bead having a thin outer layer and a core functionalized with a ligand adsorbing the mAbs or parts thereof.

26 Claims, 3 Drawing Sheets

CHROMATOGRAPHY METHOD

CROSS-REFERENCE TO RELATED APPLICATIONS

This application is a filing under 35 U.S.C. 371 of international application number PCT/EP2015/062500, filed Jun. 4, 2015, which claims priority to SE application number 1450779-2, filed Jun. 24, 2014, the entire disclosures of each of which are hereby incorporated by reference.

FIELD OF THE INVENTION

The present invention relates to a chromatography method. More closely the invention relates to a method for removal of large contaminants, such as virus, in a chromatographic process for purification of a target molecule, preferably monoclonal antibodies, mAbs, by using a specifically designed chromatographic bead having a thin outer layer and a core functionalized with a ligand adsorbing the mAbs or parts thereof.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximise the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare). More specifically, the genetic manipulation performed in the commercial recombinant protein A product is aimed at facilitating the attachment thereof to a support.

Virus removal is an essential purification step in the downstream purification of mAbs. Virus removal is conventionally performed by flowing the mAb feed through dedicated virus removal filters with a defined cut-off so the mAb passes through the filter and the main fraction of virus will not pass.

In spite of the existing technologies for virus removal during immunoglobulin production, there is still a need of improved products and processes.

SUMMARY OF THE INVENTION

In a first aspect, the invention relates to a method for purification of immunoglobulin containing proteins or parts thereof, from larger contaminants, such as virus, comprising: a) contacting an immunoglobulin containing sample with chromatography beads comprising a thin lid with a defined pore size and an inner core of defined pore size provided with an affinity ligand; b) adsorbing the immunoglobulin containing proteins to the ligands; c) washing the beads to remove any contaminants; and d) eluting the beads to release the captured immunoglobulin containing proteins or parts thereof.

The average diameter size of the chromatography bead is 10-500 µm, such as 10-50 µm, 50-100 µm or 250-450 µm. The chromatography beads may be used for, for example, polishing, capture and in midstream after cell culture.

The size of the chromatographic bead is chosen according to the specific applications needed for, for example, high resolution or fast mass transport or when the viscosity of the feed is high. The average size of the chromatography media is for example calculated as volume-weighted median diameter.

The thickness of the lid is 1-8 µm, preferably 3-5 µm. The lid thickness can be advantageously varied in accordance with the total bead size. For example, in some embodiments it is desirable to have a thinner lid in order to maintain a high binding capacity. In other embodiments, when the virus log reduction is more important than the binding capacity, it can be advantageous to design the chromatographic media with a thicker lid.

The lid is preferably inactive, i.e. not provided with any interacting ligands when a mAb or Fab is the target. The lid thickness may be measured by confocal microscopy, by microtome sectioning or conventional microscopy.

The pore size of the lid and core corresponds to a $K_D$ of 0.1 to 1, preferably 0.3 to 0.7, measured with dextran of Mw 110 kDa as the probe molecule. The invention is suitable for target molecules larger than 20 000 D, such as a Mab of about 150 000 D. The pore size has importance for the capacity but also for the selectivity. In swelling materials like agarose and other polysaccharide gels, the pore size is best estimated by an inverse size exclusion chromatography method, where the volume fraction $K_d$ accessible for a probe molecule, e.g. dextran of Mw 110 kDa, is determined. This method is described in e.g. L Hagel et al: J Chromatogr A 743, 33-42 (1996).

The pore size of the lid and core may be the same or different. For purification of Mabs and Fabs it is preferably the same.

In preferred embodiments the porosity of the lid and core is 0.30 to 0.95, preferably about 0.60 to 0.85. The porosity of the lid and core may be the same or different.

Porosity or pore density differences in the lid and core can be obtained by variations of the conditions of production of the chromatographic media such as for example the use of different amount and percentage of bead material, cross-linker, salt and shrinkage. The porosity of the chromatographic media can also be modified by selective addition in the different layers of the bead particle of different charged or uncharged chemical entities that will physically and chemically decrease the porosity.

According to the invention the lid and core are made of agarose but may also be made of other natural or synthetic polymers.

Preferably the affinity ligand is a proteinaceus affinity ligand, most preferably the ligand is Protein A or affinity ligand derived from Protein A. The ligand may be a monomer, dimer or any multimer. For Mabs the ligand is preferably a pentamer (Z4).

In another embodiment the affinity ligand is Protein L or an affinity ligand derived from Protein L. In this case the immunoglobulin is monoclonal antibodies with other structures than naturally occurring antibodies, for example monospecific antibodies (fragment antigen-binding, F(ab')2 fragment, Fab fragment, single-chain variable fragment, di-scFv, single domain antibody).

In a further embodiment the affinity ligand is Protein G or an affinity ligand derived from Protein G.

The chromatography beads may be provided in a column and the contaminants are obtained in the flow through. Alternatively, the chromatography beads are provided in a batch mode. The chromatography beads may be magnetic. In a further alternative the chromatography beads are provided in fluidised bed mode.

The method according to the invention is especially suitable for removal of contaminating virus from a Mab feed. In downstream processing of antibodies there is a demand to investigate and insure that viruses that could be present in the feed are removed. This is a key issue to obtain an official approval such as for example from FDA. Effective step for virus removal greatly simplifies the validation of the process. The method of the invention may preferably be used in a validation process for obtaining a therapeutic drug/protein, especially Mabs, free from contaminating virus.

As will be shown in the example section the method of the invention provides greatly improved virus reduction compared to prior art methods.

It is understood that the term "immunoglobulin containing proteins" embraces antibodies and fusion proteins or conjugates comprising an antibody portion or Fc chain as well as antibody fragments, such as FAbs, and mutated antibodies, as long as they have substantially maintained the binding properties of an antibody. The immunoglobulin containing proteins can be monospecific or bispecific (trifunctional antibody, chemically linked F(ab')2, bi-specific T-cell engager). The antibodies can be monoclonal antibodies or polyclonal antibodies. Preferably the antibodies are IgG, IgA and/or IgM, from a mammalian species, such as a human.

The terms chromatographic media, chromatographic bead, gel or resin are encompassing the same concept and are used interchangeably.

DETAILED DESCRIPTION OF THE INVENTION

Figure 1:
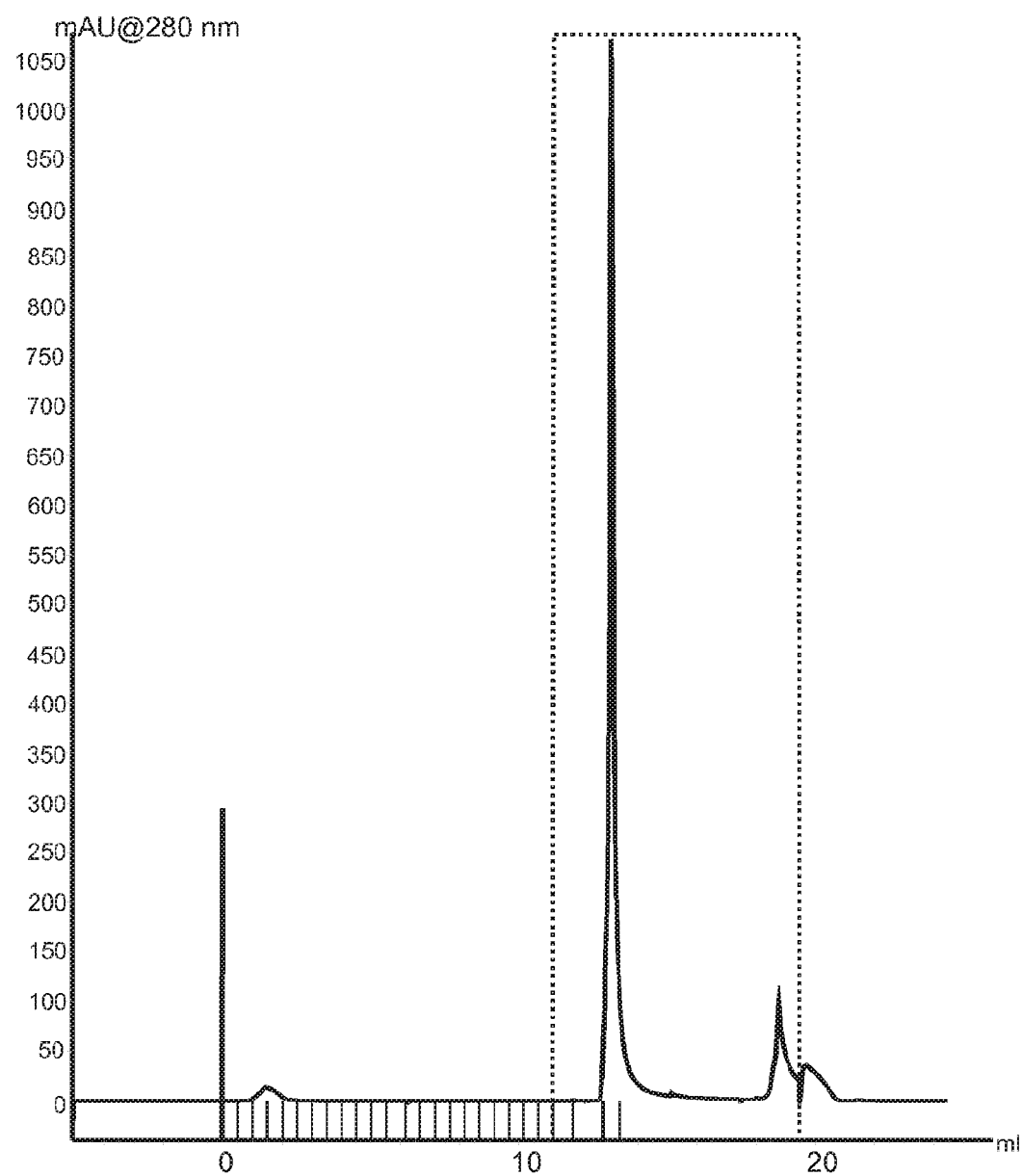
FIG. 1 shows a chromatogram for trial 1 described below, where 1 mg pure mAb and $1.2 \times 10^7$ pfu virus was injected onto prototype LS-02213C.

According to a preferred embodiment of the present invention viruses are removed in the mAb capture step by using chromatography beads with a thin inactive lid with a defined pore size and an adsorptive ligand inside the core of bead. This will make it impossible for the virus to penetrate the lid and eventually virus in the feed will come in the flow-through fraction while the mAb will diffuse through the lid layer and adsorb to the ligand inside the core of the bead.

After column wash, the mAb is then eluted traditionally with acetic acid.

The invention will now be described more closely in association with the drawings and an experimental part.

In this invention two chromatographic bead prototypes were synthesized: Protein A core bead with inactive outer layer and the protein A (Z4) ligand inside the bead, called prototypes LS-02213A, B and C.

Protein L core bead with inactive outer layer and the protein L ligand inside the bead, called prototype LS-002480.

Bacteriophage Φx174 (*Escherichia coli* bacteriophage ATCC® 13706-1™) was used as test virus. This virus is challenging to remove from the mAb by size exclusion because of its small diameter, 25 nm. The virus particle has an icosahedral structure.

Bacteriophage Φx174 infects and propagate in *Escherichia coli* (*E. coli*). Detection of Φx174 can be done by the plaque agar overlay assay with *E. coli* as host. This assay is extremely sensitive since it can detect one single virus particle.

In this invention, Φx174 was propagated in ATCC® 13706™ *E. coli* strain C (also purchased from ATCC). The phage was purified and a mAb sample was spiked with the bacteriophage. This sample was loaded onto a chromatography column containing the Core bead with inactive layer and the affinity ligand inside the bead. The column was washed after sample application and finally the mAb was eluted. During chromatography, fractions were collected to determine virus titer in selected fractions. Virus titer was determined in the flow-through fractions, first wash fractions and the mAb elution fractions. The log-reduction of virus was calculated for the mAb elution fraction.

EXPERIMENTAL PART

Example 1: Production of Lid/Core Bead

Partial bromination and lid inactivation of allylated high flow agarose (HFA), prepared according to U.S. Pat. No. 6,602,990, 30 μmol allyl/mL gel, Kd: 0.675, d50v: 87.6, Dw: 70.3

The HFA bead was inactivated in the outer layer to form three different lid thickness sizes 2, 4 and 6 μm.

Partial Bromination

The amounts of bromine added are calculated for lids 0.5 μm larger than the lid thicknesses aimed for. The reason for this is that experience shows that the lids usually become thinner than aimed for due to bromine losses.

A (2 μm lid): 60 mL of allylated HFA 35Z from LS-001647A was washed 5×GV with distilled water and then transferred drained to a 1 L round bottom flask. 450 mL of distilled water was added and mechanical propeller stirring was applied. A solution of 15 μL bromine in 100 mL distilled water was prepared in a 100 mL E-flask with magnetic stirring. The bromine solution was then added during ~60 seconds under vigorous stirring (200 rpm). The flask was left at room temperature for 15 minutes. The gel was then washed 12×GV with distilled water.

B (4 μm lid): 160 mL of allylated HFA 35Z from LS-001647A was washed 5×GV with distilled water and then transferred drained to a 2 L round bottom flask. 1200 mL of distilled water was added and mechanical propeller stirring was applied. A solution of 68 µL bromine in 100 mL distilled water was prepared in a 100 mL E-flask with magnetic stirring. The bromine solution was then added during ~60 seconds under vigorous stirring (300 rpm). The flask was left at room temperature for 15 minutes. The gel was then washed 12×GV with distilled water.

C (6 µm lid): 60 mL of allylated HFA 35Z from LS-001647A was washed 5×GV with distilled water and then transferred drained to a 1 L round bottom flask. 450 mL of distilled water was added and mechanical propeller stirring was applied. A solution of 35 µL bromine in 100 mL distilled water was prepared in a 100 mL E-flask with magnetic stirring. The bromine solution was then added during ~60 seconds under vigorous stirring (300 rpm). The flask was left at room temperature for 15 minutes. The gel was then washed 12×GV with distilled water.

Inactivation of Activated Lid

A (2 µm lid): The partially activated gel from A above was transferred drained to a 500 mL round bottom flask. 53.7 mL of distilled water and 6.34 mL of 50% NaOH (1 M) were added and mechanical propeller stirring was applied. The flask was immersed into a water bath at 50° C. for 14.5 h. The gel was then washed 10×GV with distilled water.

B (4 µm lid): The partially activated gel from B above was transferred drained to a 500 mL round bottom flask. 143.1 mL of distilled water and 16.9 mL of 50% NaOH (1 M) were added and mechanical propeller stirring was applied. The flask was immersed into a water bath at 50° C. for 14.5 h. The gel was then washed 10×GV with distilled water.

C (6 µm lid): The partially activated gel from C above was transferred drained to a 500 mL round bottom flask. 53.7 mL of distilled water and 6.34 mL of 50% NaOH (1 M) were added and mechanical propeller stirring was applied. The flask was immersed into a water bath at 50° C. for 15 h. The gel was then washed 10×GV with distilled water.

Titration

The gel was washed with plenty of water. 1.0 mL gel was measured with a Teflon cube and transferred to a suction flask with 9 mL of distilled water. A saturated solution of bromine in water was added until a yellow color due to an excess of $Br_2$ was persisting. The sample was left with magnetic stirring for 5 min. The sample was put under vacuum (water suction) with magnetic stirring to remove the excess of bromine. The sample was then transferred to a titration beaker by rinsing the flask with 10 mL of distilled water. 2-3 drops of conc. $HNO_3$ were added and titration with 0.1 M $AgNO_3$ for indirect measurement of allyl content was started. The results are given as µmol/mL gel.

| Prototype | Lid thickness µm | Titration 1 µmol/ mL gel | Titration 2 µmol/ mL gel | Remaining allyl content, µmol/ mL gel | Actual lid thickness by using remaining allyl, µm |
|---|---|---|---|---|---|
| LS-001647A Start gel #1 | | 29.51 | 30.11 | 29.81 (Full allyl) | |
| LS-001647A Start gel #2 | | 25.20 | 24.96 | 25.08 (Full allyl) | |
| LS-001840A | 2 | 19.88 | 21.05 | 20.47 | 2.5-3 |
| LS-001840B | 4 | 19.58 | 19.53 | 19.56 | 3.5 |
| LS-001840C | 6 | 17.84 | 17.64 | 17.74 | 4.5-5 |

The allylated gel LS-001647A was titrated again (#2) at the same time as the remaining allyl contents were determined. This time a lower allyl content was determined, 25.1 instead of 29.8 µmol allyl/mL gel. All added amounts of bromine for the partial activations have been calculated based on the originally determined allyl content of LS-001647A, i.e. 29.8 µmol allyl/mL gel. The actual lid thicknesses have been estimated by using the remaining allyl contents and the starting allyl content of 25.1 µmol/mL gel. The lid thicknesses didn't become quite those that were aimed for but still three different levels were obtained which was satisfying. The lid thickness can be detected using confocal microscopy.

Example 2: Construction of Protein a Core Bead

In this example Protein A was immobilized into the core of allylated HFA with different lid inactivations.

As Protein A ligand tetramer of Protein Z was used, Z (N3A, N6D, N23T)$_4$-Cys, below called Z4.

Activation of Gel

Same procedure was used for LS-001840A, B and C.

55 mL (g) of drained gel was placed into an E-flask with 55 mL of distilled water and 2.2 g of NaOAc. The flask was swirled whereafter a saturated aqueous solution of bromine was added until a yellow color was persisting. Sodium formiate was then added to quench the excess of bromine.

Reduction of Protein

To 55 mL of Z4 (51.7 mg/mL based on AAA), 570 mg $NaHCO_3$ (should have been 465 mg), 58 mg $Na_2CO_3$, 481 mg NaCl and 20 mg EDTA, were added. The E-flask was shaked and 212 mg of DTE was added and the flask was then put onto a shaking table. Reduction proceeded for 90 minutes before filling the super loop.

Desalting

A Sephadex G-25 column (~400 mL) connected to an ÄKTA system was used to desalt the tetramer. Before starting the run the column was equilibrated with 0.15 M NaCl/1 mM EDTA until conductivity and pH were stable. 52 mL of the reduced solution yielded 90.18 g of desalted tetramer. Fractions 9-17 were collected (~90 mL).

Determination of Protein Concentration by UV

The desalted solution was diluted 20× and had an absorbance of 0.286 at 276 nm. This equals a protein concentration of 26.4 mg/mL (87% yield).

Coupling

The activated gels were washed with 3×GV 0.1 M phosphate/1 mM EDTA pH 8.6.

A: 51 mL gel (LS-001840A)+14 mg Z4/mL gel (27.1 mL)+10.5 mL desalting buffer (should have been 8.615 mL)+1.45 M $Na_2SO_4$ (17.86 g) were mixed in a 250 mL flask.

B: 51 mL gel (LS-001840B)+15 mg Z4/mL gel (29.0 mL)+6.68 mL desalting buffer+1.45 M $Na_2SO_4$ (17.86 g) were mixed in a 250 mL flask.

C: 51 mL gel (LS-001840C)+16 mg Z4/mL gel (31.0 mL)+4.74 mL desalting buffer+1.45 M $Na_2SO_4$ (17.86 g) were mixed in a 250 mL flask.

Mechanical propeller stirring was applied and the flasks were immersed into a water bath at 33° C. for 3 h.

Deactivation

The gels were washed 3×GV with distilled water. The gels+1 GV 0.1 M phosphate/1 mM EDTA/7.5% thioglycerol pH 8.5 were mixed and the flasks were left at room temperature for 17 h. The gels were then washed 3 times alternately with 1×GV 0.5 M HAc and 2×GV 0.1 M TRIS/ 0.15 M NaCl pH 8.5 and then 10×GV mL with distilled water.

Drying Method

The dry weight of the prototype was determined by a single measurement. 1 mL of gel was measured using a Teflon cube and transferred to a pre-dried and pre-weighed glass filter. The gel was sucked dry and washed two times with acetone. Drying was performed in an oven at 50° C. under vacuum overnight and the dry weight of the gel was determined by subtracting the mass of the pre-weighed glass filter.

Amino Acid Analysis 1 mL of each gel was dried and analysed.

| | |
|---|---|
| LS-002213A Dry weight: 81.9 mg/mL | Ligand density: 3.8 mg/mL |
| LS-002213B Dry weight: 83.5 mg/mL | Ligand density: 5.0 mg/mL |
| LS-002213C Dry weight: 82.4 mg/mL | Ligand density: 5.0 mg/mL |

Example 3: Construction of Protein L Core Beads

Immobilization of Protein L into the core of allylated HFA with 3.5 μm lid inactivation.
Ref: Structure of Peptostreptococcal Protein L and Identification of a
Repeated Immunoglobulin Light Chain-binding Domain, The Journal of Biological Chemsitry, Vol. 267, No. 18, Issue of Jun. 25, pp. 12820-12825, 1992, William Kastem, Ulf Sjobring, and Lars Björck.

Activation of Gel 55 mL (g) of drained gel from LS-001840B was placed into an E-flask with 55 mL of distilled water and 2.2 g of NaOAc. The flask was swirled whereafter a saturated aqueous solution of bromine was added until a yellow color was persisting. Sodium formiate was then added to quench the excess of bromine.

Coupling

The activated gel was washed with 3×GV 0.2 M phosphate/1 mM EDTA pH 11.5. 52 mL gel (LS-001840B)+15 mg PrL/mL gel (15.2 mL)+21.2 mL coupling buffer+1.30 M Na$_2$SO$_4$ (16.32 g) were mixed in a 250 mL flask.

Mechanical propeller stirring was applied and the flask was immersed into a water bath at 30° C. for 17.5 h.

Deactivation

The gel was washed 3×GV with distilled water and then 4×GV with 0.1 phosphate/1 mM EDTA pH 8.5. The gel+1 GV 0.1 M phosphate/1 mM EDTA/7.5% thioglycerol pH 8.5 were mixed and the flask with stirring was immersed into a water bath at 45° C. for 2 h. The gel was then washed 3 times alternately with 3×GV 0.1 M HAc and 3×GV 0.1 M TRIS/ 0.15 M NaCl pH 8.5 and then 10×GV mL with distilled water.

Drying Method

The dry weight of the prototype was determined by a single measurement. 1 mL of gel was measured using a Teflon cube and transferred to a pre-dried and pre-weighed glass filter. The gel was sucked dry and washed two times with acetone. Drying was performed in an oven at 50° C. under vacuum overnight and the dry weight of the gel was determined by subtracting the mass of the pre-weighed glass filter.

Amino Acid Analysis, AAA 1 mL of gel was dried and analysed.

| | |
|---|---|
| LS-002480 Dry weight: | 91.4 mg/mL gel |
| Ligand density: | 11.9 mg PrL/mL gel |
| Multipoint attachment: | 10.6 lysines/PrL attached to the gel |

The AAA data for the amino acids alanine, valine, isoleucine and leucine are used when calculating ligand density and degree of multipoint attachment.

Experiment 4: Propagation of Bacteriophage and Bacteria

Nutrient Agar 23 g nutrient agar and 5.0 g NaCl was weighed into a 1000 mL glass beaker. The glass beaker was filled with 1000 milli-Q water and the solution was mixed. The solution was autoclaved for 15 min at 121° C. After autoclaving, the solution was stored in a 45° C. water bath.

Nutrient Broth 16 g nutrient broth and 5.0 g NaCl was weighed into a 1000 mL glass beaker. The glass beaker was filled with 1000 mL milli-Q water and the s solution was mixed. The solution was autoclaved for 15 min at 121° C. After autoclaving, the solution was stored in a 45° C. water bath.

Top Agar 7.7 g nutrient agar and 5.0 g NaCl was weighed into a 1000 mL glass beaker. The glass beaker was filled with 1000 milli-q water and the solution was mixed. The solution was autoclaved for 15 min at 121° C. After autoclaving, the solution was stored in a 45° C. water bath.

Preparation of Agar Plates 10 cm plates were prepared by adding 10 mL of the 45° C. nutrient agar into each plate. The plates were stored at 5° C.

1 mL nutrient broth was added into the freeze dried vial from ATCC containing *Escherichia coli* strain C. 50 μL glycerol was also added and the vial was mixed well. The vial was stored at −70° C.

To propagate bacteria, a serological loop was placed into the freezed bacteria and some bacteria was catched on the loop. The loop, containing bacteria, was drawn on an agar plate. The agar plate was placed overnight in a 37° C. incubator. Next day bacterial growth was seen on the agar plate and the bacteria was scraped off by a serological loop and put into a tube containing 3 mL nutrient broth. The tube was incubated in an environmental shaker for 18 h and a hazy development of bacterial growth was developed after 18 hours.

1 mL of the nutrient broth was pipetted into the freeze dried vial containing the *Escherichia coli* bacteriophage ATCC® 13706-01™ (Φ×174). A 10 cm agar plate was pre-warmed for 1 hour at 37° C. Two drops of the 3 mL bacteria culture was mixed with 2.5 mL top agar. This aliquot was poured onto the pre-warmed plate and the plate was leaved to solidify. 0.5 mL of the re-hydrated phage solution was pipetted serologically onto the surface of the top-agar in the agar plate. The agar plate was incubated over-night and lysis of *E. coli* cells was seen. The soft agar surface was scraped off into a sterile 10 mL centrifugal tube. The suspension was centrifuged at 4000 rpm for 10 minutes and the supernatant was sterile filtrated through a 0.2 μm sterile filter into a sterile 1.5 mL collection tube. The propagated and filtrated phage solution in the tube was stored at 5° C.

To determine the virus titer of the propagated phage solution, a plaque overlay assay was used.

Bacteria was propagated as above but when growing the cells in the broth tube, the growth was stopped after 3 hours. 8 agar-plates were pre-warmed at 37° C. The phage was serially diluted in sterile 1.5 mL tubes by pipetting 10 µL of the phage stock and mix with 990 µL nutrient broth. This was the $10^2$ dilution.

The phage was further serially diluted up to $10^9$ by taking 100 µL of each dilution and mix with 900 µL nutrient broth.

100 µL of each dilution of phage was mixed with 300 µL bacteria in a 10 mL sterile centrifuge tube, incubated for 15 minutes and then 3 mL of warm (45° C.) top-agar was added to every tube. The top agar mixed with the bacteria and phages were poured onto the agar plates. The top agar was solidified in room temperature and put into the 37° C. incubator for 3 hours. After 3 hours visible 3-5 mm plaques could be seen and at certain dilutions these plaques were countable in a colony counter. 17 plaques were found in the $10^7$ dilution which means that the concentration of virus in the stock was $17 \times 10^7/0.1$ ml $= 17 \times 10^8 = 1.7 \times 10^9$ pfu (plaque forming units)/mL.

Example 5: Virus Removal from mAb Sample by Chromatography

| | |
|---|---|
| Chromatography system | ÄKTA avant 25 sn 1536118, GE Healthcare |
| Column | Tricorn 5/100, GE Healthcare |
| Resin | LS-02213C Core Bead 4.5-5 µm OH-lid Ligand: 5.0 mg Z4/mL gel Base matrix: HFA |
| Reference resin | MabSelect SuRe LX, GE Healthcare |

Samples:

mAb, pure 3.0 mg/mL, purified with Mabselect SuRe, Capto S to remove acid and basic variants and Capto adhere to remove HCP and DNA mAb 5, semi purified 15.0 mg/mL, only purified with MabSelect SuRe Trial 1

15 µL phage stock ($1.7 \times 10^9$ pfu/mL), 1.0 mL of 3.0 mg/mL pure mAb in PBS and 0.48 mL PBS solution was mixed in a 1.5 mL tube. The solution was sterile filtrated using a 0.2 µm sterile filter. This was the start material. Note that sterile filtration might reduce the amount of bacteriophages. Trial 1 was performed on prototype of the invention.

Trial 2 and 3

50 µL phage stock ($1.7 \times 10^9$ pfu/mL), 1.0 mL of 15 mg/mL of PrA purified Mab (not pure) and 3.95 mL PBS solution was mixed in a 10 mL centrifuge tube. The solution was filtrated through a 0.45 µm filter. This was the start material. Note that 0.45 µm filtration might reduce the amount of bacteriophages. Trial 2 was performed on prototype of the invention. Trial 3 is a comparative example performed on a commercial resin.

Chromatograhy

Two tricorn columns were packed with prototype LS-002213C at at flow-rate of 8 mL/min in 10 mM NaCl. The bed-height was adjusted to 5.2 cm and the top adaptor was adjusted ~1 mm below the mark. 1.0 mL resin in the column was obtained. Same packing procedure was performed for the MaB Select SuRe LX resin.

The system flow was checked at 1.0 mL/min using a 10 mL volumetric flask. The columns were equilibrated for 5 cv at 0.25 mL/min (4 mm residence time). 500 µL of the Mab mix with bacteriophage was injected onto each column using a 500 µL capillary loop. Fraction collection with 0.5 mL fractions were started.

After injection, the column was washed with 5 cv PBS at 0.25 mL/min followed by 5 cv 0.1 M NaOAc pH 6.0 at 0.25 mL/min. The mAb was eluted with 5 cv 0.1 M HAc at 0.25 mL/min and the fraction collector only peak fractionated the elution peak using the watch commandos Peak start >50 mAU, peak End <100 mAU. The column was CIP:ed with 2 cv 0.1 M NaOH at 0.25 mL/min (including a 20 mm hold after 1 cv) followed by a 5 cv equilibration with PBS at 0.25 mL/min.

The mAb elution peak in fractions b10 and b11 were pooled (if needed).

Virus Counting

Bacteria was propagated as above but at 9 mL scale. The growth was stopped after 3 hours. 90 agar-plates were pre-warmed at 37° C. Each fraction selected and start sample was serially diluted in sterile 1.5 mL tubes by pipetting 100 µL of the fraction and mix with 900 µL nutrient broth. The samples was further serially diluted up to $10^7$ by taking 100 µL of each dilution and mix with 900 µL nutrient broth.

100 µL of each dilution of sample was mixed with 300 µL bacteria in a 10 mL sterile centrifuge tube, incubated for 15 minutes and then 3 mL of warm (45° C.) top-agar was added into each tube. The top agar mixed with the bacteria and phages were poured onto the agar plates. The top agar was solidified in room temperature and put into the 37° C. incubator for 3 hours. After 3 hours visible 3-5 mm plaques could be seen and at certain dilutions these plaques were countable in a colony counter.

Results

FIG. 1 shows the chromatogram from trial 1, where 1 mg pure mAb mixed with phages was injected onto prototype LS-02213C. Selected fractions for plaque overlay assay: Start sample, A1, A2, A3, A4 and mAb elution peak B10 and B11 (pooled volume=0.56 mL).

The protocol for counting plaques (pfu) can be seen in Table 1. Bold figures are the number that have been used for calculation.

TABLE 1

Pfu counting protocol of selected fractions from the chromatogram at different dilutions, trial 1.

| Dilution | Start sample Pfu | Fraction A1 Pfu | Fraction A2 pfu | Fraction A3 pfu | Fraction A4 pfu | mAb elution peak B10, B11 pfu |
|---|---|---|---|---|---|---|
| $10^1$ | N/A | — | — | — | — | 18 |
| $10^2$ | N/A | — | — | — | — | 1 |
| $10^3$ | — | — | — | — | 106 | 0 |
| $10^4$ | >100 | >100 | 50 | 29 | 8 | 0 |
| $10^5$ | 24 | 11 | 2 | 4 | — | N/A |
| $10^6$ | 2 | 1 | 0 | 0 | — | N/A |
| $10^7$ | 0 | 0 | 1 | 0 | — | N/A |

Mass balance calculations, trial 1:
Start sample: $2.4 \times 10^6$ pfu/$0.1 \times 0.5 = 1.2 \times 10^7$ pfu loaded
A1: $1.1 \times 10^6/0.1 \times 0.5 = 5.5 \times 10^6$ pfu
A2: $5.0 \times 10^5/0.1 \times 0.5 = 2.5 \times 10^6$ pfu
A3: $2.9 \times 10^5/0.1 \times 0.5 = 1.45 \times 10^6$ pfu
A4: $8 \times 10^4/0.1 \times 0.5 = 0.4 \times 10^6$ pfu
Total in A1-A4=$9.85 \times 10^6$ pfu, Yield=0.985/1.20*100=82%
Elution fraction: $1.8 \times 10^2/0.1 \times 0.56$ mL=$1.0 \times 10^3$ pfu
Reduction: $\log_{10} (1.2 \times 10^7/1.0 \times 10^3) = 4.1$
Mab Yield: Mab loaded 1.0 mg, mAb eluted in pool=90.83 mg Yield=83% (measured by UV at 280 nm using ext.coeff. of 1.4)

Figure 2:
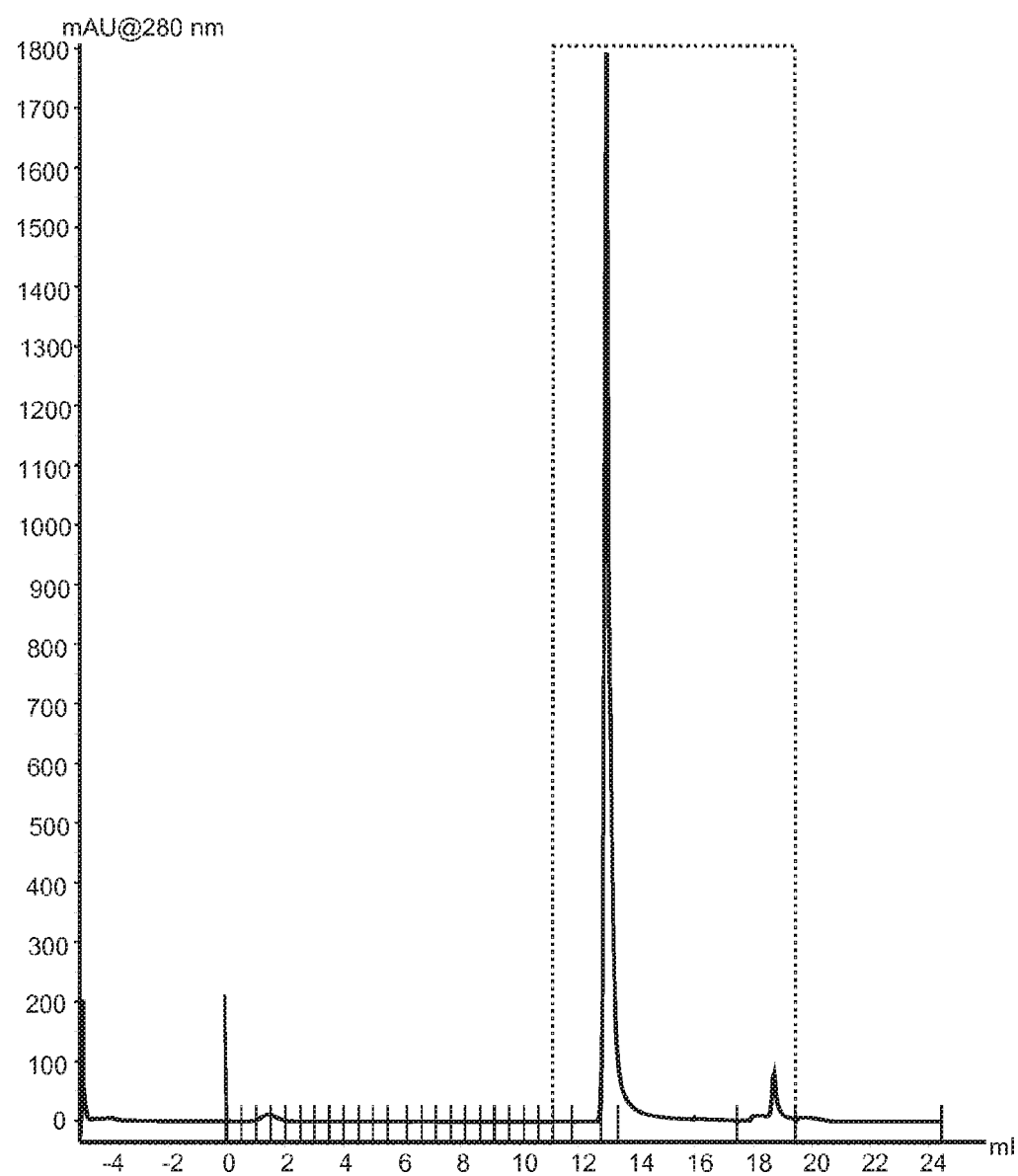
FIG. 2 shows the chromatogram for trial 2 where 1.5 mg semi-purified mAb mixed with phages was injected onto prototype LS-02213C.

FIG. 2 shows the chromatogram for trial 2 where 1.5 mg semi-purified mAb and $2.8 \times 10^7$ pfu was loaded onto prototype LS-02213C.

The protocol for counting plaques (pfu) for trial 2 can be seen in Table 2. Bold figures are the number that have been used for calculation.

TABLE 2

Pfu counting protocol of selected fractions from the chromatogram at different dilutions, trial 2.

| Dilution | Start sample pfu | Fraction A1 pfu | Fraction A2 pfu | Fraction A3 pfu | Fraction A4 pfu | Fraction A5 pfu | mAb elution peak B10, B11 pfu |
|---|---|---|---|---|---|---|---|
| $10^1$ | N/A | N/A | N/A | N/A | N/A | >100 | >100 |
| $10^2$ | N/A | N/A | N/A | N/A | N/A | >100 | 53 |
| $10^3$ | N/A | 73 | >100 | >100 | >100 | >100 | 5 |
| $10^4$ | >100 | 11 | 50 | 32 | 25 | 16 | 0 |
| $10^5$ | 56 | 2 | 8 | 5 | 4 | 0 | N/A |
| $10^6$ | 5 | N/A | N/A | 0 | 0 | N/A | N/A |
| $10^7$ | 0 | N/A | N/A | 0 | 0 | N/A | N/A |

Mass balance calculations, trial 2:
Start sample: $5.6 \times 10^6$ pfu/$0.1 \times 0.5 = 2.8 \times 10^7$ pfu loaded
A1: $1.1 \times 10^5/0.1 \times 0.5 = 0.55 \times 10^6$ pfu
A2: $5.0 \times 10^5/0.1 \times 0.5 = 2.5 \times 10^6$ pfu
A3: $3.2 \times 10^5/0.1 \times 0.5 = 1.6 \times 10^6$ pfu
A4: $2.5 \times 10^5/0.1 \times 0.5 = 1.25 \times 10^6$ pfu
A5: $1.6 \times 10^5/0.1 \times 0.5 = 0.8 \times 10^6$ pfu
Total in A1-A5=$0.67 \times 10^7$ pfu, Yield=0.67/2.8*100=24%
Elution fraction: $5.3 \times 10^3/0.1 \times 0.58$ mL=$3.1 \times 10^4$ pfu
Reduction: $\log_{10}(2.8 \times 10^7/3.1 \times 10^4) = 3.0$
Mab Yield: Mab loaded 1.5 mg, mAb eluted in pool=1.34 mg Yield=89% (measured by UV at 280 nm using ext.coeff. of 1.4)

Figure 3:
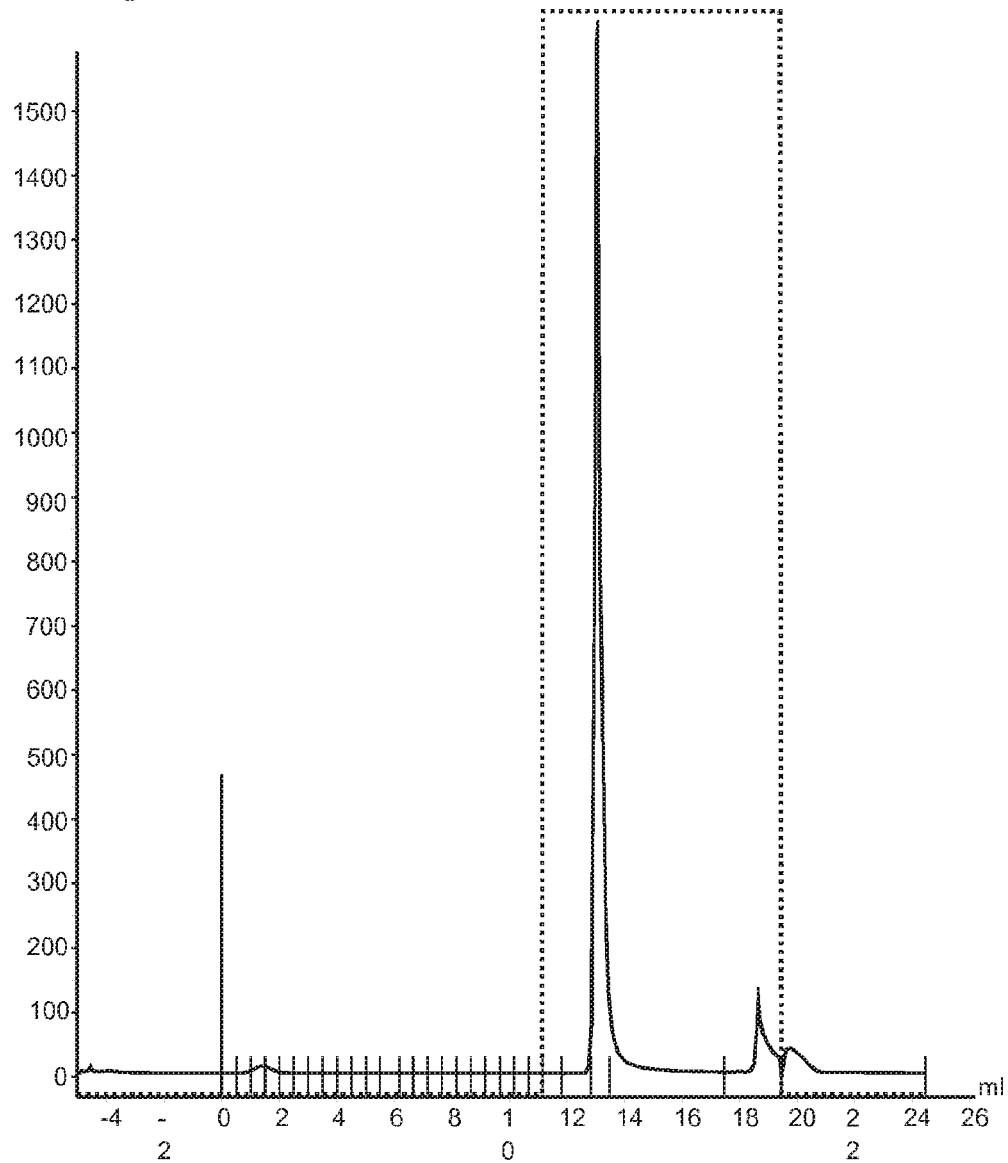
FIG. 3 shows a chromatogram where 1.5 mg semi-purified mAb mixed with phages was injected onto a commercial chromatography resin, MabSelect Sure LX.

FIG. 3 shows the chromatogram were 1.5 mg semi-purified mAb mixed with phages was injected onto MabSelect Sure LX. Selected fractions for plaque overlay assay: Start sample, A1, A2, A3, A4, A5 and mAb elution peak.

In the chromatogram of FIG. 4, 1.5 mg semi-purified mAb and $1.4 \times 10^7$ pfu was loaded onto MaBSelect SuRe LX.

TABLE 3

Pfu counting protocol of selected fractions from the chromatogram at different dilutions, trial 3.

| Dilution | Start sample pfu | Fraction A1 pfu | Fraction A2 pfu | Fraction A3 pfu | Fraction A4 pfu | Fraction A5 pfu | mAb elution peak B10, B11 pfu |
|---|---|---|---|---|---|---|---|
| $10^1$ | N/A | N/A | N/A | N/A | N/A | >100 | >100 |
| $10^2$ | N/A | N/A | N/A | N/A | N/A | >100 | >100 |
| $10^3$ | N/A | N/A | >100 | >100 | >100 | 35 | 24 |
| $10^4$ | >100 | 3 | 22 | 24 | 10 | 1 | 0 |
| $10^5$ | 28 | 0 | 6 | 3 | 1 | 0 | N/A |
| $10^6$ | 3 | N/A | N/A | 0 | 0 | 0 | N/A |
| $10^7$ | 0 | N/A | N/A | 0 | 0 | 0 | N/A |

Mass balance calculations, trial 3:
Start sample: $2.8 \times 10^6$ pfu/$0.1 \times 0.5 = 1.4 \times 10^7$ pfu loaded
A1: $0.3 \times 10^5/0.1 \times 0.5 = 0.15 \times 10^6$ pfu
A2: $2.2 \times 10^5/0.1 \times 0.5 = 1.1 \times 10^6$ pfu
A3: $2.4 \times 10^5/0.1 \times 0.5 = 1.2 \times 10^6$ pfu
A4: $1.0 \times 10^5/0.1 \times 0.5 = 0.5 \times 10^6$ pfu
A5: $0.35 \times 10^5/0.1 \times 0.5 = 0.17 \times 10^6$ pfu
Total in A1-A5=$3.1 \times 10^6$ pfu, Yield=0.31/1.4*100=22%
Elution fraction: $2.4 \times 10^4/0.1 \times 0.66$ mL=$1.6 \times 10^5$ pfu
Reduction: $\log_{10}(1.4 \times 10^7/1.6 \times 10^5) = 1.9$
Mab Yield: Mab loaded 1.5 mg, mAb eluted in pool=1.36 mg Yield=91% (measured by UV at 280 nm using ext.coeff. of 1.4)

Results

For pure mAb the virus reduction was 1 log better than for the trial using semi-purified mAb for prototype LS-02213C. The virus recovery was also better (82%) in the trial where pure mAb has been used in comparison to the trial where semi-purified mab has been used (only 24%).

In trial 2 and 3, where same start material was used, using the semi-purified mAb feed it was clearly shown-that the prototype LS-02213C had better virus reduction performance than MabSelect SuRe. The prototype LS-02213C showed 1 log better virus reduction than MabSelect SuRe.

The result show that the prototype LS-02213C was able to reduce the amount bacteriophage with a log reduction of 4.1 and with a mAb yield of 83%, using a pure mAb.

Using a semi-purified mAb the log virus reduction was 3.0 for LS-02213C and 1.9 for MabSelect Sure LX.

It should be noted that the log reduction is dependent on residence/adsorption time (flow rate) and wash volume before eluting the protein. In the above examples, a standard column residence time, 4 min, and a standard wash of 10 column volumes (prior elution) was used.

The invention claimed is:

1. A method for purification of immunoglobulin containing proteins or parts thereof, from contaminants that are larger than immunoglobulin containing proteins, the method comprising:

a) contacting an immunoglobulin containing sample with agarose chromatography beads comprising a lid consisting of agarose modified with hydrolyzed allyl groups and having a thickness of 1-8 µm with a defined pore size and an inner core of defined pore size consisting of agarose modified with an affinity ligand;
b) adsorbing the immunoglobulin containing proteins to the ligands;
c) washing the beads to remove any contaminants; and
d) eluting the beads to release the captured immunoglobulin containing proteins or parts thereof.

2. The method of claim 1, wherein the contaminants are virus.

3. The method of claim 1, wherein the average diameter size of the chromatography bead is 10-500 µm.

4. The method of claim 1, wherein the thickness of the lid is 3-5 µm.

5. The method of claim 1, wherein the pore size of the lid and core correspond to Kd of 0.1 to 1.

6. The method of claim 1, wherein the porosity of the lid and core is 0.30 to 0.95.

7. The method of claim 1, wherein the affinity ligand is a proteinaceus affinity ligand.

8. The method of claim 1, wherein the ligand is Protein A or affinity ligand derived from Protein A.

9. The method of claim 1, wherein the immunoglobulin containing protein is a mAb.

10. The method of claim 1, wherein the affinity ligand is Protein L or an affinity ligand derived from Protein L.

11. The method of claim 1, wherein the immunoglobulin is a Fab.

12. The method of claim 1, wherein the affinity ligand is Protein G or an affinity ligand derived from Protein G.

13. The method of claim 1, wherein the chromatography beads are provided in a column and the contaminants are obtained in the flow through.

14. The method of claim 1, wherein the chromatography beads are provided in a batch mode.

15. The method of claim 1, wherein the chromatography beads are magnetic.

16. The method of claim 1, wherein the chromatography beads are provided in fluidised bed mode.

17. The method of claim 1, which is used in a validation process for obtaining therapeutic immunoglobulins substantially free from contaminating virus.

18. A method for purification of immunoglobulin containing proteins or parts thereof from virus, the method comprising:
a) contacting an immunoglobulin containing sample with chromatography beads comprising a lid having a thickness of 3-5 µm with a defined pore size and an inner core of defined pore size provided with protein Z4 ligand;
b) adsorbing the immunoglobulin containing proteins to the ligands;
c) washing the beads to remove any virus; and
d) eluting the beads to release the captured immunoglobulin containing proteins or parts thereof, which are substantially free from contaminating virus,
wherein the average diameter size of the chromatography bead is 250-450 µm,
wherein the pore size of the lid and core correspond to $K_D$ of about 0.3 to 0.7,
wherein the porosity of the lid and core is 0.60 to 0.85, and
wherein the lid and core are made of agarose.

19. The method of claim 18, wherein the lid consists of agarose modified by hydrolyzed allyl groups.

20. The method of claim 18, wherein the immunoglobulin containing protein is a mAb.

21. The method of claim 18, wherein the immunoglobulin is a Fab.

22. The method of claim 18, wherein the chromatography beads are provided in a column.

23. The method of claim 18, wherein the chromatography beads are provided in a batch mode.

24. The method of claim 18, wherein the chromatography beads are magnetic.

25. The method of claim 18, wherein the chromatography beads are provided in fluidised bed mode.

26. The method of claim 18, which is used in a validation process for obtaining therapeutic immunoglobulins substantially free from contaminating virus.

* * * * *